(12) United States Patent
Klima et al.

(10) Patent No.: US 6,273,876 B1
(45) Date of Patent: Aug. 14, 2001

(54) CATHETER SEGMENTS HAVING CIRCUMFERENTIAL SUPPORTS WITH AXIAL PROJECTION

(75) Inventors: Daniel J. Klima, Plymouth; Paul J. Thompson, New Hope; Robert M. Vidlund, Maplewood, all of MN (US)

(73) Assignee: IntraTherapeutics, Inc., St. Paul, MN (US)

( * ) Notice: Subject to any disclaimer, the term of this patent is extended or adjusted under 35 U.S.C. 154(b) by 0 days.

(21) Appl. No.: 09/185,769

(22) Filed: Nov. 3, 1998

Related U.S. Application Data

(63) Continuation-in-part of application No. 08/986,054, filed on Dec. 5, 1997, now abandoned.

(51) Int. Cl.⁷ .................................................. A61M 5/00
(52) U.S. Cl. ............................................................ 604/264
(58) Field of Search ........................... 604/264, 523–526; 600/434, 585

(56) References Cited

U.S. PATENT DOCUMENTS

| | | |
|---|---|---|
| 4,516,972 | 5/1985 | Samson . |
| 4,955,862 | 9/1990 | Sepetka . |
| 5,095,915 | 3/1992 | Engelson . |
| 5,178,158 | 1/1993 | de Toledo . |
| 5,190,520 * | 3/1993 | Fenton, Jr. et al. ................... 604/43 |
| 5,380,304 | 1/1995 | Parker . |
| 5,448,989 * | 9/1995 | Heckele ............................... 604/142 |
| 5,454,795 | 10/1995 | Samson . |
| 5,507,751 | 4/1996 | Goode et al. . |
| 5,507,766 | 4/1996 | Kugo et al. . |
| 5,569,200 | 10/1996 | Umeno et al. . |
| 5,573,520 | 11/1996 | Schwartz et al. . |
| 5,599,326 | 2/1997 | Carter . |
| 5,658,264 | 8/1997 | Samson . |
| 5,662,622 * | 9/1997 | Gore et al. ............................ 604/282 |
| 5,681,263 | 10/1997 | Flesch . |
| 5,702,373 * | 12/1997 | Samson ................................ 604/282 |
| 5,931,830 * | 8/1999 | Jacobsen et al. ..................... 604/523 |

FOREIGN PATENT DOCUMENTS

| | | |
|---|---|---|
| 41 13 265 A1 | 3/1992 | (DE) . |
| 92 18 100 | 8/1993 | (DE) . |
| 44 14 810 C1 | 8/1995 | (DE) . |
| 298 07 045 U1 | 8/1998 | (DE) . |
| 0 439 931 A1 | 8/1991 | (EP) . |
| 0 626 604 A2 | 11/1994 | (EP) . |
| 0 670 169 A2 | 9/1995 | (EP) . |
| 0 782 836 A1 | 7/1997 | (EP) . |
| WO 93/15785 | 8/1993 | (WO) . |
| WO 95/33507 | 12/1995 | (WO) . |
| PCT/US96/38193 | 5/1996 | (WO) . |

* cited by examiner

Primary Examiner—Manuel Mendez
(74) Attorney, Agent, or Firm—Merchant & Gould P.C.

(57) ABSTRACT

The present disclosure relates to a segment of catheter having a longitudinal axis extending between distal and proximal ends of the catheter segment. The segment includes a plurality of circumferential supports surrounding the longitudinal axis. The segment also includes axially members connected to the circumferential supports. The axial members extend in the direction generally along the longitudinal axis. The axial members include three ends that are positioned between the circumferential supports.

21 Claims, 11 Drawing Sheets

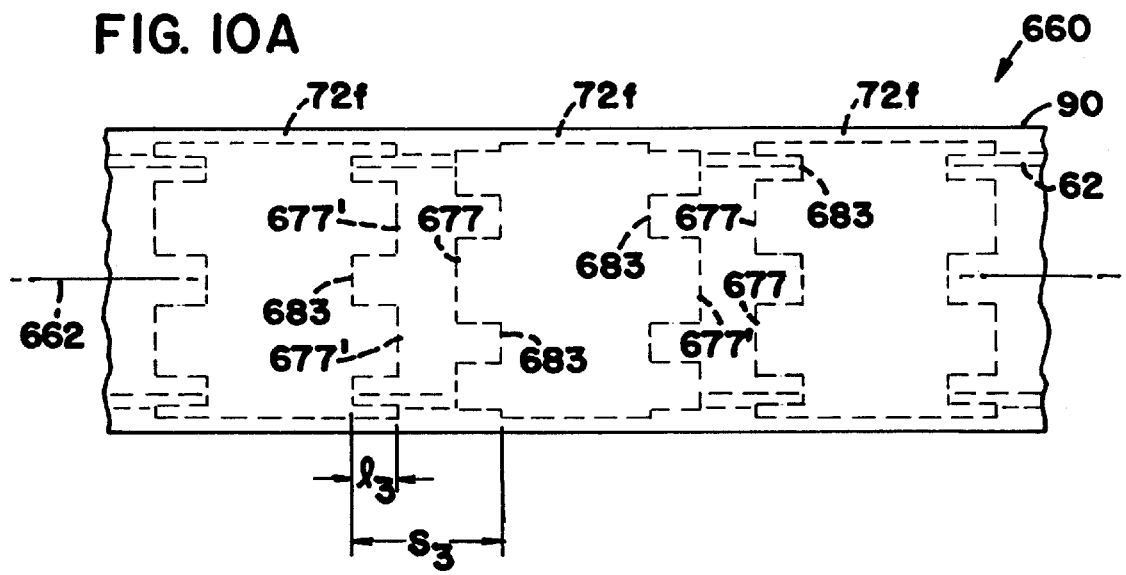
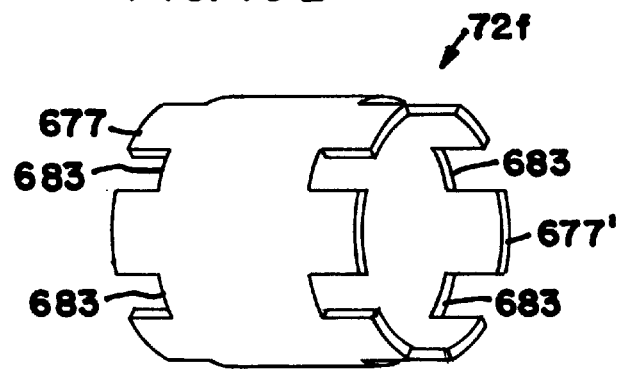

US 6,273,876 B1

CATHETER SEGMENTS HAVING CIRCUMFERENTIAL SUPPORTS WITH AXIAL PROJECTION

CROSS REFERENCE TO RELATED APPLICATIONS

This application is a continuation-in-part of U.S. Pat App. Ser. No. 08/986,054 which was filed Dec. 5, 1997, now abandoned.

GOVERNMENT SUPPORT

This invention was made with Government support under Small Business Independent Research Grant HL60320, awarded by the National Institutes of Health. The Government has certain rights in the invention.

BACKGROUND OF THE INVENTION

1. Field of the Invention

This invention pertains to catheters for passage through a vasculature system. More particularly, this invention pertains to a novel construction of at least a segment of a catheter.

2. Description of the Prior Art

Catheters are widely used in medical treatment. A catheter is an elongated flexible member advanced through the vasculature system to a desired site. The catheter may be advanced over a previously inserted guide wire.

With the catheter in place, a wide variety of substances may be passed through the catheter to the site. For example, drugs may be moved through the catheter for site—specific drug delivery. Also, implements may be passed through the catheter. The catheter may also be used to remove fluids from the site. Still further, a catheter may be equipped with implements (e.g., balloon tips) for performing procedures (e.g., angioplasty) at the site.

Catheters have long been used in cardiovascular treatment. More recently, catheters are used in neurological procedures requiring advancement of the catheter through very narrow vessels. To accomplish these advances, a high degree of flexibility is desired. Also, catheters need very thin walls in order to retain an internal bore having as large a diameter as possible.

While advancing a catheter, a physician may twist a proximal end of the catheter in order to cause a corresponding twist of the distal end of the catheter (referred to as "torque transmission response"). A consistently reliable torque transmission response (e.g., a consistent one-to-one torque transmission response) is desired.

In designing catheters, it is desirable to provide a catheter which is kink resistant. Namely, a catheter typically is a tube with an internal bore of circular cross-section. When a catheter bends, it may be inclined to kink resulting in closure or geometric deformation of the circular bore. Such closure or deformation is undesirable. Further, in certain applications, the catheter may be subjected to high internal pressures (e.g., 300 psi). Such pressures tend to burst the catheter or expand the catheter geometry.

In neurological applications, catheters preferably have extremely flexible distal tips. While a high degree of flexibility is desired, flexibility should be attained while retaining burst strength and without undue sacrifice of torque transmission response.

In certain applications, the distal tip of a catheter may be shaped for unique purposes. For example, in treating an aneurysm, the distal tip may be shaped to have a radial projection so the tip more easily enters and remains in the aneurysm when reaching the site. A common practice is to shape the tip through steam application. The steam application softens the polymer lining at the tip permitting it to be bent and retain a bent shape following the steam application. Where the distal tip is supported by a traditional coil or braid construction, the tip may not adequately retain the bent shape since the coil or braid is inclined to resume its unbent shape against the resistance of the polymer.

SUMMARY OF THE INVENTION

A general aspect of the present invention relates to a segment of a catheter. The catheter includes a longitudinal axis extending between distal and proximal ends of the catheter. The segment of the catheter includes a plurality of circumferential supports surrounding the longitudinal axis. Axial members are connected to the circumferential supports. The axial members extend in a direction generally along the longitudinal axis and include free ends positioned between the circumferential supports.

BRIEF DESCRIPTION OF THE DRAWINGS

FIG. 10A is a side elevation view of a catheter segment having of a sixth embodiment of a circumferential support according to the present invention;

FIG. 10B is a perspective view of one of the circumferential supports used by the embodiment of FIG. 10A in isolation from the catheter segment;

DETAILED DESCRIPTION OF THE PREFERRED EMBODIMENT

Referring now to the several drawing figures in which identical elements are numbered identically throughout, a description of a preferred embodiment of the present invention will now be provided.

Figure 1:
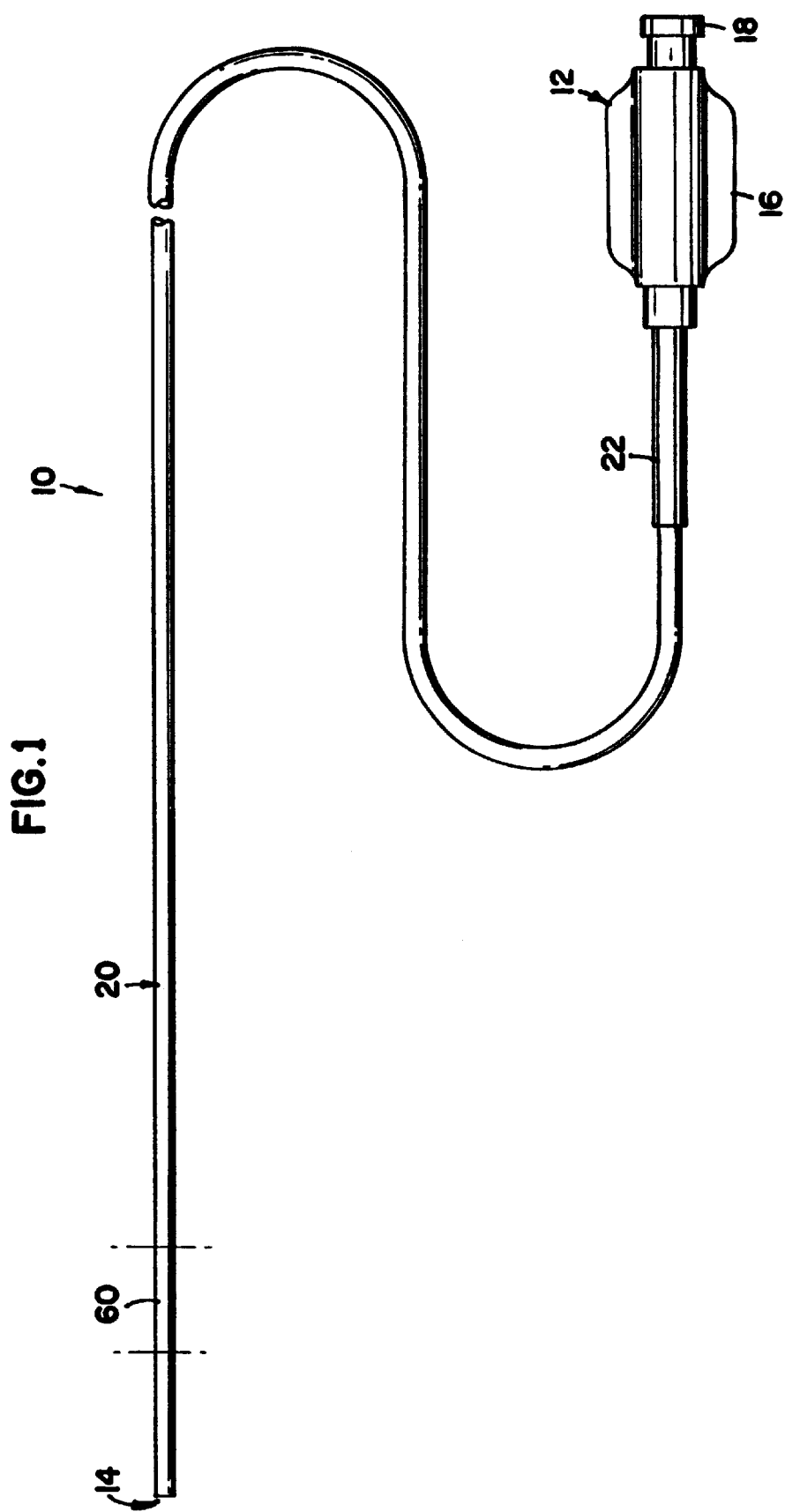
FIG. 1 is an overall view of a catheter according to the present invention.

FIG. 1 illustrates a catheter 10. The catheter 10 extends from a proximal end 12 to a distal end 14. At the proximal end 12, a hub 16 is provided to be gripped by a physician as well as having an inlet 18 for injection of fluids into the catheter 10. A flexible hollow shaft 20 is connected to the hub 16. The shaft 20 is sized to be inserted into a patient's vasculature. The shaft 20 is commonly about 150 cm long. A strain relief jacket 22 connects the shaft 20 to the hub 16. The foregoing description forms no part of this invention and is given to facilitate an understanding of the present invention.

The catheter 10 includes a segment 60 having the novel construction of the present invention. (For purposes of the remainder of this description, the word "catheter" is generally used to refer to the flexible shaft 20 of FIG. 1 having the segment 60 which a construction as will be described.) While the entire length of the catheter 10 can be constructed as will be described with reference to segment 60, it may be desirable to have a catheter 10 of multiple segments of different construction to impart different properties to different regions of the catheter 10 along its length. For example, it may be desirable to provide a catheter 10 having a proximal portion stiffer than a more flexible distal portion. While the present invention is suitable for forming catheter segments of varying degrees of flexibility and other properties, the present invention is described with reference to a segment 60 of the length of the catheter 10. This is to allow for catheters where the entire length is constructed according to the teachings of this application as well as catheters where only a discrete portion is so constructed and where the remainder is constructed according to conventional catheter construction techniques.

Figure 2:
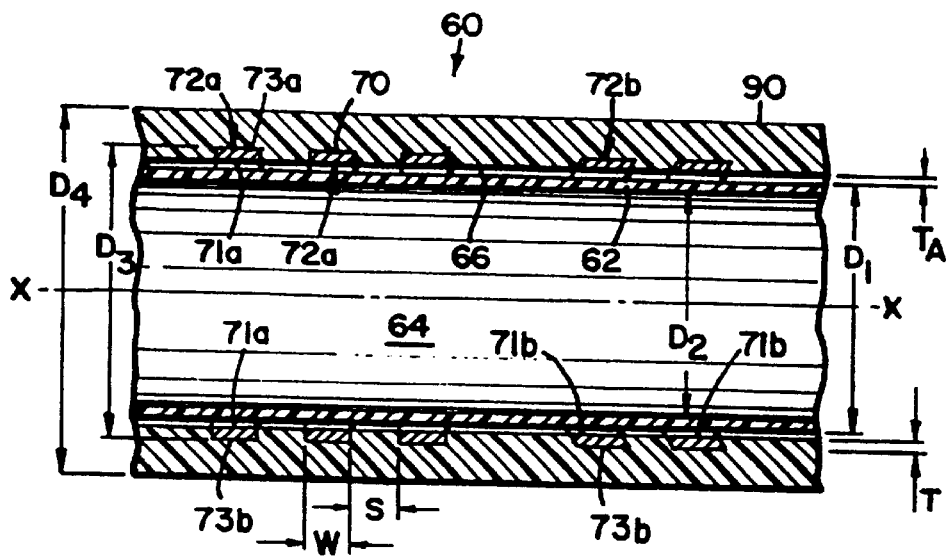
FIG. 2 is a cross-sectional, longitudinal view of a longitudinal segment of the catheter of FIG. 1.
Figure 3:
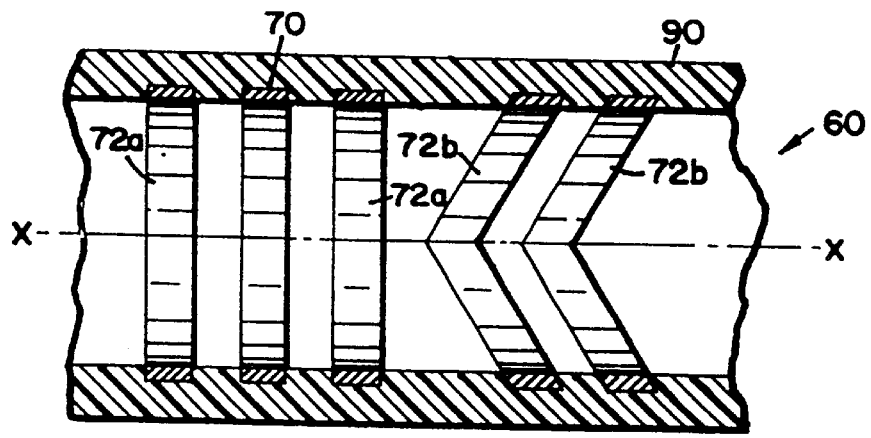
FIG. 3 is the view of FIG. 2 with an inner liner removed to expose only circumferential supports according to the present invention and to expose an outer liner.

With reference to FIGS. 2 and 3, the segment 60 is shown to illustrate the novel construction. The segment 60 is a multi-layer construction including a flexible inner layer 62. By way of non-limiting example, the inner layer 62 is polytetraflouroethylene (PTFE) more commonly known by the trademark Teflon®. In a preferred embodiment, layer 62 has an outer diameter $D_1$ of 0.0230 inch (0.58 mm) and an inner diameter $D_2$ of 0.0210 inch (0.53 mm) to define an internal bore 64 surrounded by the Teflon inner tube layer 62.

The segment 60 also includes a novel support structure 70 as will be more fully described. The support structure 70 is generally tubular and can be adhered to the external surface of the inner layer 62 by a thin bonding layer of any suitable adhesive 66 (e.g., polyurethane having a thickness $T_A$ of about 0.0004 inch or 0.01 mm). The support structure 70 has an outer diameter $D_3$ of about 0.025 inch (0.635 mm).

Surrounding the exterior of the support structure 70, an outer polymer jacket 90 is provided. The outer jacket 90 may be any suitable flexible material for use in the vascular system. Such materials may be nylon or urethane. The outerjacket 90 has an outer diameter $D_4$ of 0.029 inch (0.74 mm).

In the foregoing, Applicants have provided a specific description of various layers of segment 60 as well as describing specific materials and dimensions. Such specificity has been given to describe a preferred embodiment of a specific catheter 10 utilizing the novel support structure 70 as will be described. More or fewer layers of materials could be used with structure 70 to impart desired properties (e.g., varying stiffness, strength, etc.) to segment 60. Similarly, specific materials and dimensions may be varied to alter the properties of segment 60.

Referring now to FIG. 3, the novel support structure 70 of the present invention will now be described. The support structure 70 includes a plurality of circumferential supports 72a, 72b. Each of the supports 72a, 72b is a ring surrounding the axis X—X. The supports 72a, 72b differ in shape for reasons that will be described. FIG. 3 illustrates that different shaped supports 72a, 72b may be included within segment 60 to alter properties (e.g., flexibility or torque transmission response along the length of segment 60). Alternatively, segment 60 could include circumferential supports which are of identical construction along its length (e.g., all having the shape of supports 72a) to impart more uniform properties to segment 60 along its length.

The circumferential supports 72a, 72b are positioned in parallel, spaced-apart alignment about axis X—X. Adjacent supports 72a, 72b are disjointed. Namely, each support 72a, 72b is an independent ring of rigid material. There is no rigid material (e.g., the material of rings 72a, 72b) interconnecting the rings 72a, 72b. Instead, adjacent rings are interconnected only by the flexible material of the liners 62, 90. Therefore, the rings 72a, 72b are non-integrally connected. As a result of the disjointed alignment of rings 72a, 72b, the segment 60 is highly flexible with the rings 72a, 72b providing structural integrity to retain the cross-sectional geometry of bore 64.

By way of example, the circumferential supports 72a, 72b have a width W of about 0.003 inch (0.076 mm). The width is the dimension parallel to the axis X—X. The circumferential supports 72a, 72b have a thickness T of about 0.001 inch (0.025 mm) (ie., the radial dimension measured between the inner and outer surfaces 71a, 71b and 73a, 73b of the circumferential supports 72a, 72b). Finally, the circumferential supports 72a, 72b have an axial spacing S between opposing/adjacent supports 72a, 72b of about 0.005 inch (0.127 mm). Preferably, the support structure 70 is fabricated from a solid blank of medical grade stainless steel tubing. Other possible materials includes nickel-titanium alloys (e.g., nitinol) and cobalt-chromium-nickel alloys (e.g., Elgiloy™ alloy of Elgiloy, Inc. of Elgin, Ill., U.S.A.). Such a fabrication process includes starting with a rod (not shown) having an outer diameter equal to the desired inner diameter of the PTFE layer 62. The PTFE layer 62 is placed over the rod which acts as a jig to hold the elements of catheter 10 during fabrication. The adhesive 66 is applied to the external surface of PTFE layer 62. A solid tube of medical grade stainless steel (referred to as a hypotube) is then adhered to PTFE layer 62 by adhesive 66. As an alternative, the PTFE layer 62 and the metal tube can be assembled without the adhesive 66 with parts held in alignment until the final outer layer 90 is applied.

The solid metal tube is then milled to remove excess material of the tube as waste and leaving only the material of the circumferential supports 72a, 72b as the support structure 70. In a preferred embodiment, the metal tube is milled by a chemical milling process. In such a process, a pattern mask of the desired pattern of the circumferential supports 72a, 72b is placed over the metal tube. A light source sensitizes a photoresist applied to the metal to create a pattern on the metal tube matching the mask. The photosensitized tube is then chemically etched to dissolve away the areas of the tube corresponding to the waste leaving only the desired material of the circumferential supports 72a, 72b. It will be appreciated that this description of a chemical milling of the metal tube forms no part of this invention per se. Such a process is more fully described in commonly assigned and copending U.S. patent application Ser. No. 08/645,607 the specification of which was published on Dec. 5, 1996 as International Publication No. WO96/38193 on PCT International application Ser. No. PCT/US96/08232.

After the tube is so milled, the outer layer 90 is applied to the outer surface of the support structure 70. The material of the outer layer 90 may, at the option of a designer, fill in the axial spacing S between the circumferential supports 72a, 72b or leave such spacing as voids to enhance flexibility. The rod is then removed from the PTFE layer 62 leaving a completed segment 60.

Having described the structure and fabrication of the catheter segment 60 in a preferred embodiment, the benefits of the present invention will be apparent to one of ordinary skill in the art. The present invention overcomes the disadvantage of prior art coil-construction catheters.

The circumferential supports 72a, 72b increase the burst strength of the catheter 10 when used to infuse drugs or other media at high pressure (i.e., 300 psi). The rings 72a, 72b are reinforcing members resisting radial expansion forces urging the catheter toward expansion. Further, the rings 72a, 72b resisting kinking and other geometric deformation of the internal cross-section of the catheter 10.

The present invention has been described in a preferred embodiment and may be modified while keeping with the teachings of the present invention. For example, the support structure 70 need not be formed of metal or fabricated in the chemical milling manner indicated. The support structure 70 can be formed from any structural material in any manner including, without limitation, electrical discharge machining, laser cutting, or assembly of individual components.

Similarly, while a preferred support structure 70 has been disclosed, numerous modifications can be made to the structure to vary the properties of the catheter 10 to meet design objectives for a specific application. The geometry of the support rings 72a, 72b can be varied (e.g., wider, narrower, closer or more distant spacing as well as non-symmetrical shapes compared to the symmetrical shapes shown) to vary strength and flexibility.

Figure 4:
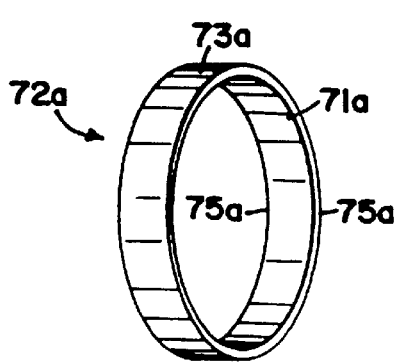
FIG. 4 is a perspective view of a first embodiment of a circumferential support according to the present invention.
Figure 5:
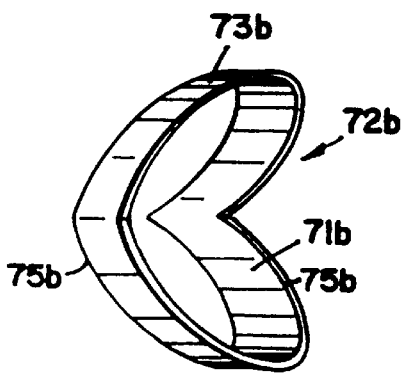
FIG. 5 is a perspective view of a second embodiment of a circumferential support according to the present invention.

FIGS. 4 and 5 illustrate two possible geometries of supports 72a, 72b. Since the supports 72a, 72b are formed by removing material from a cylindrical tube, the rings 72a, 72b are each complete circumferential surfaces surrounding the axis and are segments of a cylindrical tube. In FIG. 4, the ring 72a has parallel and planer axial ends 75a. In FIG. 5, the axial ends 75b are parallel but non-planer such that the ring 72b, in cross-section presents a V-shaped profile (see FIG. 3). Also, the circumferential supports 72a, 72b can be made narrower or thinner than the dimensions disclosed as well as changing the shape (as illustrated comparing FIGS. 4 and 5). Such modifications (as well as modifying the spacing S between supports 72a, 72b) alter the flexibility of segment 60. Therefore, the present invention provides a catheter designer with a wide variety of design options to use the present invention to fabricate catheters of varying properties for specific applications.

While the present invention is suitable for a wide variety of catheter applications, it is particularly suitable for use in so-called microcatheters used in neurological applications. Commonly, such catheters vary flexibility by varying a thickness of an outer polymeric jacket. The disconnected supports 72a, 72b of the present invention achieve flexibility while retaining a reinforced structure. This design is particularly suitable for the tip end (i.e., the final 3 cm of the distal end) of a microcatheter. Currently available microcatheters have tip ends using braids or coils. Such structures can result in the shape of the tip end relaxing during medical procedures. The present invention improves geometric integrity.

The present invention achieves enhanced flexibility without needing to narrow the thickness of a polymeric lining and without sacrificing burst strength. The invention is also particularly adapted for use in so-called flow-directed catheters where the catheter is advanced in response to fluid flow and not in response to axial forces applied at a proximal end of the catheter.

Since there is no rigid attachment between supports 72a, 72b, a reduction in torque transmission response may be possible. In the embodiment of FIG. 4, torque transmission is by the polymeric liners 90, 62 which are not as responsive as metal or other rigid material. Torque transmission is enhanced in the embodiment of FIG. 5 where the supports 72b are nested (i.e., spaced apart by only a small distance) such that in any circumferential direction, a surface of a support 72b opposes a surface of an adjacent support 72b. During torque, polymeric material of liner 90 between the opposing surfaces compresses and urges the adjacent support 72b to rotate. Further, for any given width W of the support 72b, there is an increase in surface area of the support 72b bonded to polymeric liners 90, 62 which increases torque transmission.

Figure 6:
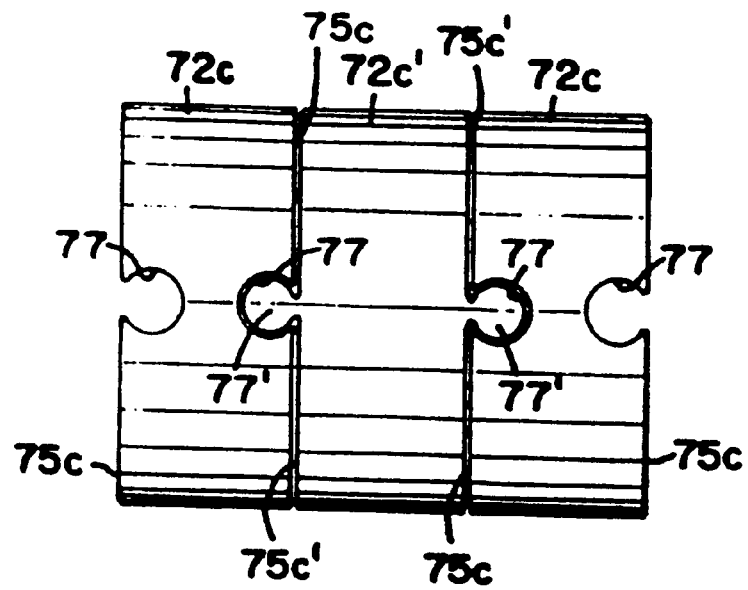
FIG. 6 is a side elevation view of a third embodiment of a circumferential support according to the present invention.
Figure 7:
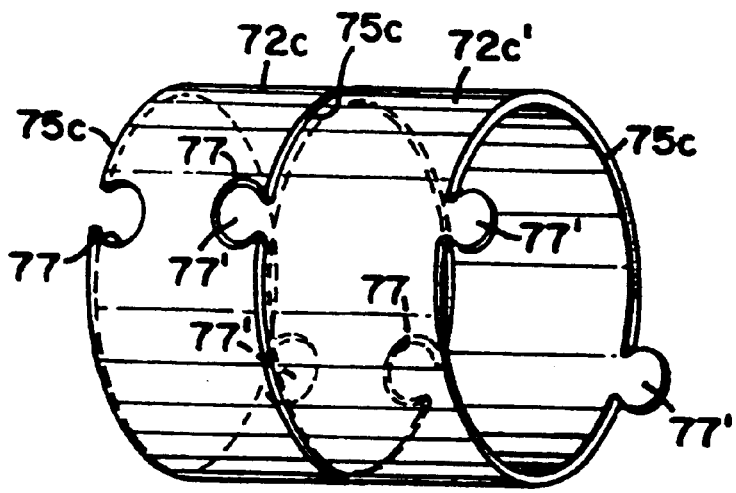
FIG. 7 is a perspective view of the embodiment of FIG. 6.

FIGS. 6 and 7 show an alternative embodiment support 72c, 72c'. Like supports 72a, 72b, supports 72c, 72c' are formed disjointed without material of the supports 72c, 72c' being interconnected. However, support 72c has keyways 77 formed into axial ends 75c. Supports 72c' are provided with complementarily shaped keys 77' extending from axial ends 75c'. The interlocking keys 77' and keyways 77 are disjointed (i.e., without material connection) to provide the enhanced flexibility of the present invention. The keyways 77 and keys 77' provide enhanced torque response by reason of compression of polymeric material between the opposing surfaces of the keyways 77 and keys 77' during torque application. Also, the interlocking keys 77' and keyways 77 increase the tensile strength of the catheter. Within the tolerance of the spacing between the opposing surfaces of the supports 72c, 72c', the supports are very flexible relative to one another. Modification of the spacing permits a catheter design to alter flexibility as desired.

Figure 8A:
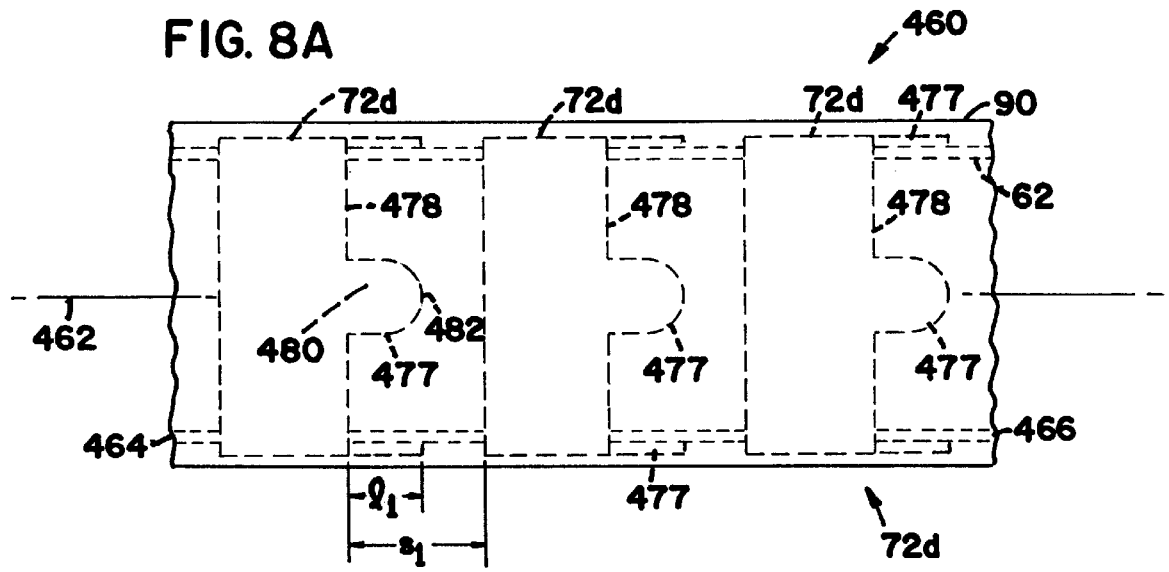
FIG. 8A is a side elevation view of a catheter segment having a fourth embodiment of a circumferential support according to the present invention.

FIG. 8A shows an alternative catheter segment 460 in accordance with the principles of the present invention. The catheter segment 460 includes a plurality of circumferential supports 72d surrounding and axially spaced along a longitudinal axis 462. Each circumferential support 72d is shown formed disjointed without material of the supports 72d being interconnected. The circumferential supports 72d surround flexible inner layer 62 and are encased within flexible outer jacket 90. The catheter segment 460 includes a distal end 464 positioned opposite from a proximal end 466.

Figure 8B:
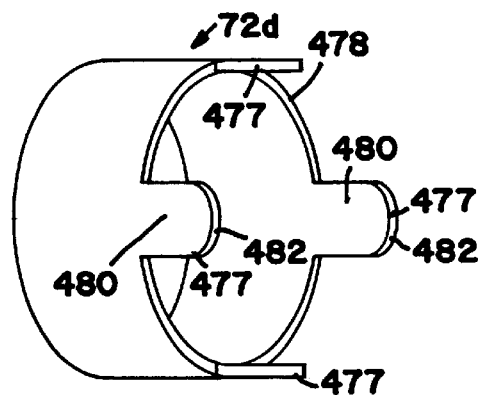
FIG. 8B is perspective view of one of the circumferential supports used by the embodiment of FIG. 8A in isolation from the catheter segment.

Referring to FIGS. 8A and 8B, axial projections 477 project axially outward from proximal ends 478 of the circumferential supports 72d. The axial projections 477 extend in a direction generally along the longitudinal axis 462. Base ends 480 of the axial projections 477 are unitarily formed with the circumferential supports 72d. Free ends 482 of the axial projections 477 are positioned opposite the base ends 480. The axial projections 477 extend in a distal direction with respect to their corresponding circumferential supports 72d such that the free ends 482 of the axial projections 477 are positioned between adjacent circumferential supports 72d. While in certain embodiments, the free ends 482 may contact adjacent circumferential supports 72d, it will be appreciated that no fixed connection preferably exists between the free ends 482 and adjacent circumferential supports 72d. In other words, the free ends 482 have a generally cantilevered configuration. The free ends 482 of the axial projections 477 are shown as being rounded, but could have other configurations.

The axial projections 477 are uniformly spaced about the circumference of the circumferential supports 72d. As shown in FIG. 8A, each of the supports 72d is positioned in the same rotational or circumferential orientation relative to the longitudinal axis 462 such that the axial projections 477 of adjacent supports 72d are in general axial alignment. For example, sets of the axial projections 477 are shown aligned along common axial lines when no axial load or torque is being applied to the segment. The projections 477 of adjacent supports could also be circumferentially staggered relative to one another.

The circumferential supports 72d are positioned in parallel, spaced apart alignment about the longitudinal axis 462. Adjacent supports 72d are disjointed. For example, each support 72d is an independent ring of relatively rigid material. There is no rigid material (e.g., the material of the rings 72d) interconnecting the rings 72d. Hence, adjacent rings are interconnected only by the flexible material of the liners 62, 90. By way of non-limiting example, the axial projections 477 can have longitudinal lengths $l_1$ in the range of 0.005–0.010 inches. Also by way of non-limiting example, an unloaded longitudinal spacing $s_1$ between adjacent circumferential supports 72d can be in the range of 0.005–0.015 inches. The term "unloaded" is intended to mean that no axial loading or torque is being applied to the catheter segment.

Figure 9A:
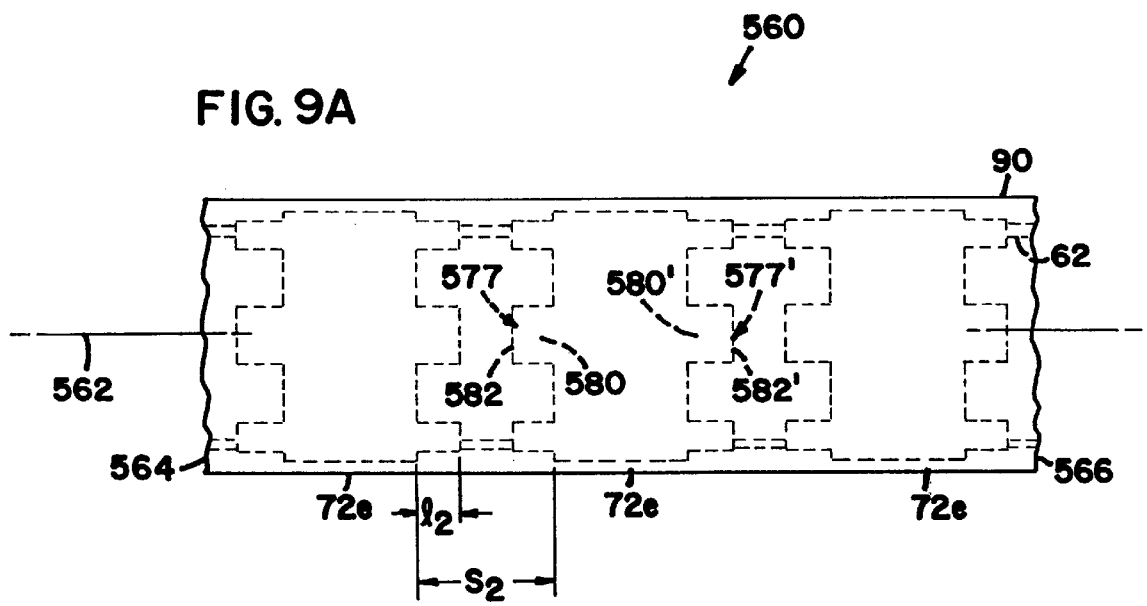
FIG. 9A is a side elevation view of a catheter segment having a fifth embodiment of a circumferential support according to the present invention.

FIG. 9A shows a further catheter segment 560 according to the present invention. The catheter segment 560 includes a plurality of circumferential supports 72e that are positioned in parallel, spaced apart alignment along a longitudinal axis 562. The longitudinal axis 562 extends between distal and proximal ends 564 and 566 of the catheter segment 560. Each circumferential support 72e is shown as an independent ring-like structure. The circumferential supports 72e are mounted on flexible inner liner 62 and flexible outer jacket 90 is formed over and between the circumferential supports 72e.

Figure 9B:
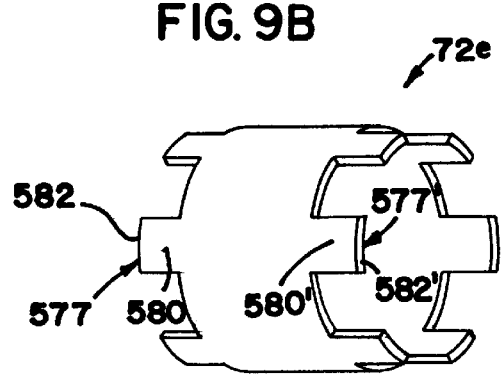
FIG. 9B is a perspective view of one of the circumferential supports used by the catheter segment of FIG. 9A in isolation from the catheter segment.

As shown in FIGS. 9A and 9B, proximal and distal projections 577' and 577 are connected to each circumferential support 72e. The proximal projections 577' extend proximally outward from the circumferential supports 72e, while the distal projections 577 extend distally outward from their corresponding circumferential supports 72e. The projections 577 and 577' include base ends 580 and 580' integrally formed with the supports 72e and free ends 582 and 582' that are positioned between adjacent circumferential supports 72e. The projections 577 and 577' are aligned generally parallel with respect to the longitudinal axis 562.

The proximal and distal projections 577' and 577 are each generally rectangular in shape. Each of circumferential supports 72e is arranged at the same rotational or circumferential orientation relative to the longitudinal axis 562. Consequently, the projections 577 and 577' of adjacent circumferential supports 72e are in general axial alignment with one another.

By way of non-limiting example, the projections 577 and 577' can have lengths $l_2$ in the range 0.005–0.010 inches. Also, an unloaded axial spacing $s_2$ in the range of 0.010–0.025 inches can exist between adjacent circumferential supports 72e.

FIG. 10A shows a side view of a catheter segment 660 that is a further embodiment of the present invention. The catheter segment 660 includes a plurality of circumferential supports 72f mounted on flexible inner liner 62 and surrounded by flexible outer jacket 90.

FIG. 10B shows a single one of the circumferential supports 72f in isolation from the liners 62 and 90. As shown in FIG. 10A, the circumferential supports 72f are positioned in parallel, spaced apart alignment along a longitudinal axis 662 and each comprise independent rings.

Distal and proximal projections 677 and 677' project axially or longitudinally outward from opposite axial ends of each circumferential support 72f. Adjacent circumferential supports 72f are disjointed. The axial projections 677 and 677' extend in a direction generally parallel to the longitudinal axis 662.

Adjacent circumferential supports 72f are positioned in different circumferential or rotational orientations about the longitudinal axis 662. For example, as shown in FIG. 10A, the projections 677 and 677' of adjacent circumferential supports 72f are not in axial alignment with one another. Instead, each axial projection 677 and 677' is in axial alignment with a gap 683 defined between axial projections 677 and 677' corresponding to an adjacent circumferential support 72f. The axial projections 677 and 677' are preferably larger than the gaps 682 to inhibit meshing between the circumferential supports 72f. In the embodiment of FIGS. 10A and 10B, the axial projections 677 and 677' preferably have lengths $l_3$ in a range of 0.005–0.010 inches, and an unloaded spacing $s_3$ of 0.010–0.025 inches preferably exists between the circumferential supports 72f.

The ring configurations depicted by FIGS. 8A and 8B, 9A and 9B and 10A and 10B cooperate to facilitate transmitting axial loads through the catheter segments while maintaining flexibility of the catheter segments. Rings provide an advantage over a coil construction in that reject rings (i.e., rings with etch defects) can be discarded prior to assembling the catheter tubing. Preferably, the rings include at least three teeth or projections so as to provide stable load transfer between the circumferential supports and to inhibit twisting of the catheter when axial loads are applied.

When an axial load is applied to one of the catheter segments 460, 560 and 660, the axial projections are compressed against adjacent circumferential supports, or against axial projections associated with the circumferential supports, thereby transferring axial load through the supports rather than through the outer jacket 90. In certain embodiments of the present invention, the outer jacket 90 may inhibit the axial projections from physically contacting adjacent circumferential supports. In such embodiments, portions of the outer jacket positioned between the axial projections and adjacent circumferential supports are compressed more than the remainder of the outer jacket. By using a configuration having circumferential supports with axial projections, the axial projections help inhibit collapsing of the catheter segment as the catheter segment is advanced through a lumen, but do not compromise the flexibility of the catheter segment.

Figure 11A:
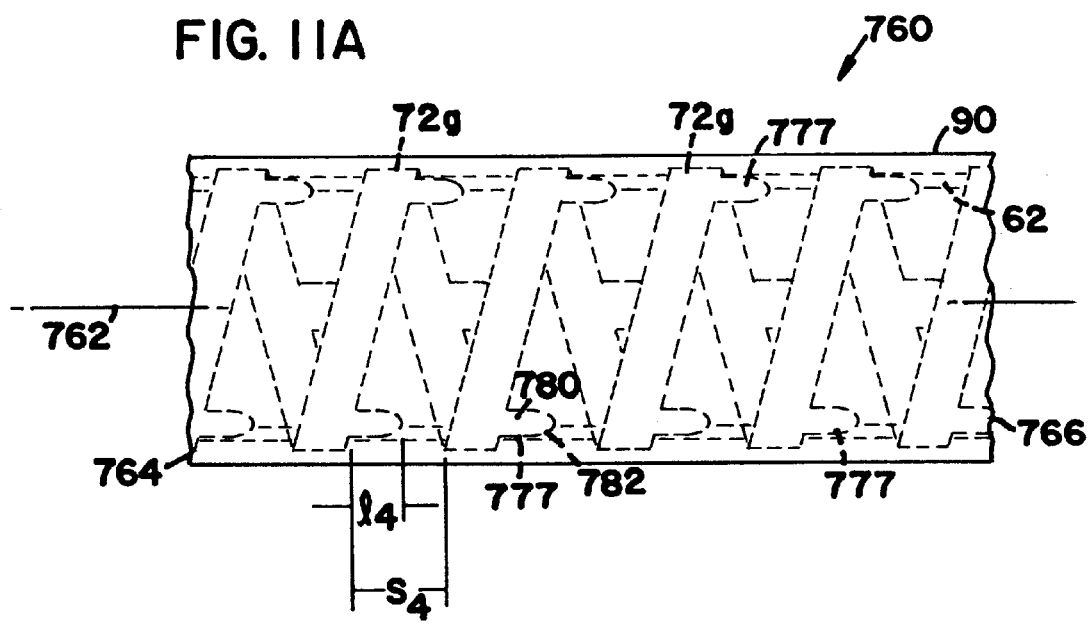
FIG. 11A is a side elevation view of a catheter segment having of a seventh embodiment of a circumferential support according to the present invention.

FIG. 11A is a side view of a catheter segment 760 that is a further embodiment of the present invention. The catheter segment 760 includes a plurality of circumferential supports 72g mounted on flexible inner liner 62. Flexible outer jacket 90 covers the inner liner 62 and encapsulates the circumferential supports 72g. The catheter segment 760 includes a distal end 764 positioned opposite a proximal end 766.

Figure 11B:
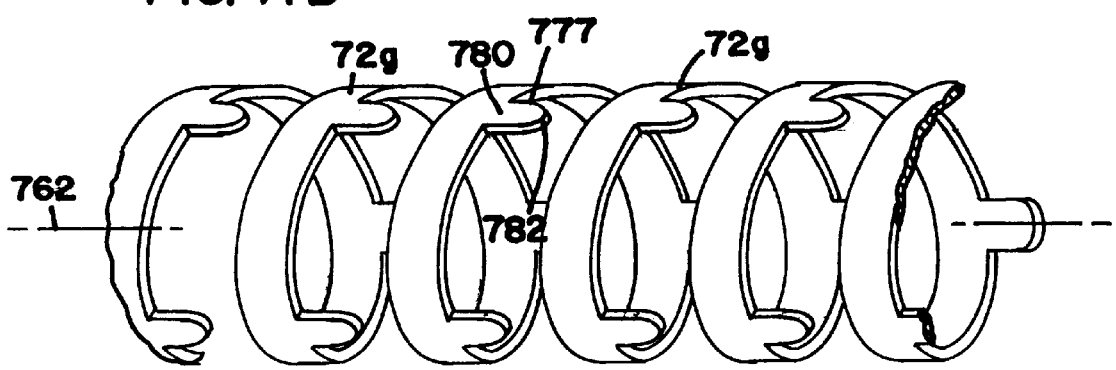
FIG. 11B is a perspective view of the circumferential support used by the embodiment of FIG. 11A in isolation from the catheter segment.

Referring to FIG. 11B, the circumferential supports 72g are shown as interconnected helical rings that wrap or extend around a longitudinal axis 762. Axial projections 777 extend distally outward from distal ends of the circumferential supports 72g. The axial projections 777 are aligned parallel to the longitudinal axis 762 and include base ends 780 integrally connected to the circumferential supports 72g and free ends 782 positioned between the circumferential supports 72g. The free ends 782 of the circumferential support 72g are rounded.

Similar to the axial projections of the previously described embodiments, the axial projections 777 assist in transferring axial force or loading through the catheter segment 760. The axial projections 777 are circumferentially spaced about the longitudinal axis 762. Also, the axial projections 777 of adjacent circumferential supports 72g can be generally axially aligned. By way of non-limiting example, the axial projections 777 can have axial lengths $l_4$ in the range of 0.005–0.010 inches, and an unloaded spacing $s_4$ in the range of 0.005–0.015 inches can be used between adjacent circumferential supports 72g.

Figure 12A:
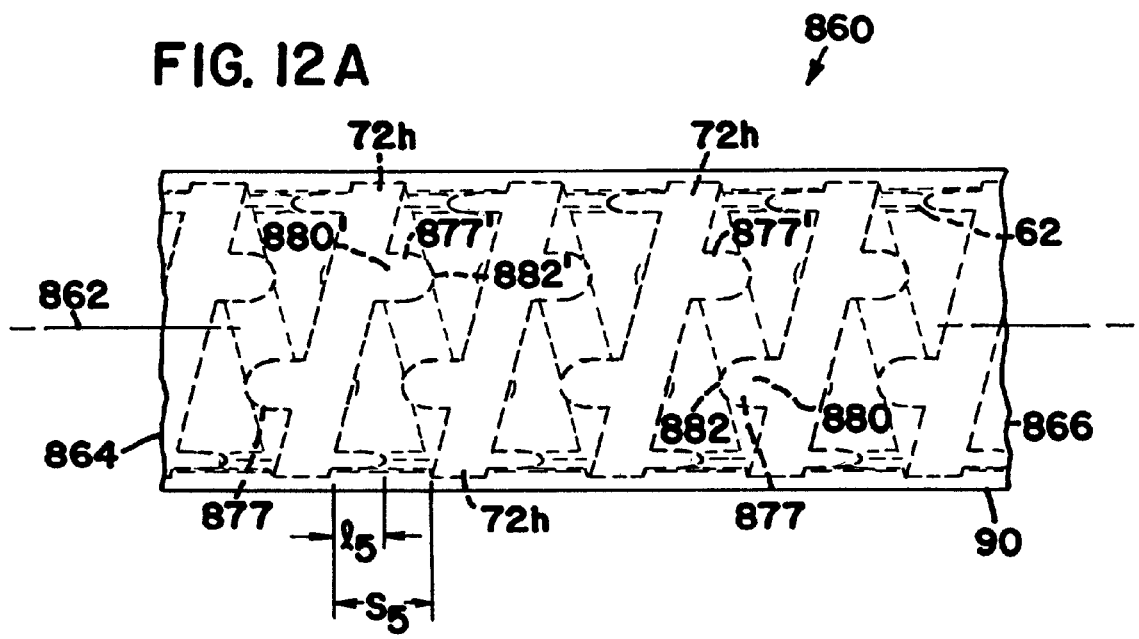
FIG. 12A is a side elevation view of a catheter segment having of an eighth embodiment of a circumferential support according to the present invention.

FIG. 12A is a side view of a catheter segment 860 that is a further embodiment of the present invention. The catheter segment 860 includes a plurality of circumferential supports 72h that are encapsulated between inner liner 62 and outer jacket 90. The circumferential supports 72h are helically coiled around a central longitudinal axis 862. The catheter segment includes a distal end 864 positioned opposite from a proximal end 866.

The catheter segment 860 includes proximal and distal projections 877' and 877 that are circumferentially spaced about the longitudinal axis 862. The proximal projections 877' extend longitudinally outward from proximal ends of the circumferential supports 72h. The distal projections 877 extend longitudinally outward from distal ends of the circumferential supports 72h. The proximal projections 877' include base ends 880' integrally connected to the proximal ends of the circumferential supports 72h. Similarly, the distal projections 877 include base ends 880 that are integrally connected with the distal ends of the circumferential supports 72h. The proximal and distal projections 877' and 877 include free ends 882' and 882 that are positioned between adjacent circumferential supports 72h.

Figure 12B:
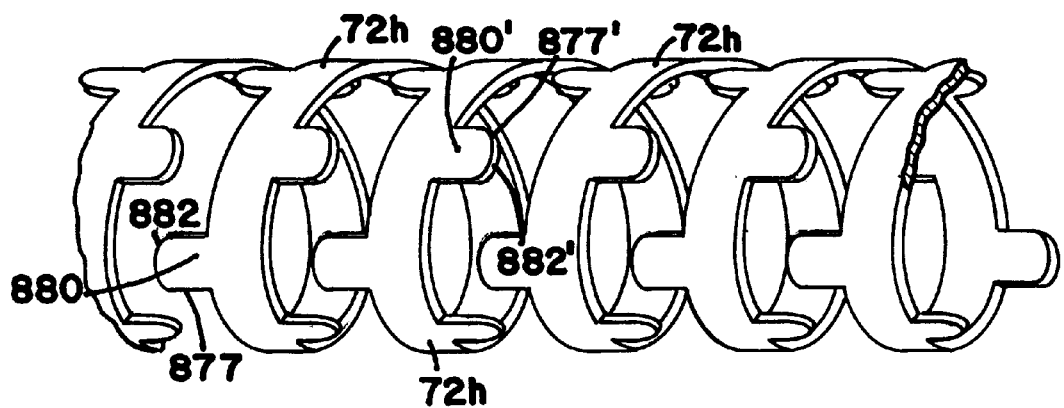
FIG. 12B is a perspective view of the circumferential support used by the embodiment of FIG. 12A in isolation from the catheter segment.

Referring to FIG. 12B, the proximal projections 877' are circumferentially staggered relative to the distal projections 877. For example, the proximal projections 877' are positioned to align between the distal projections 877 of adjacent circumferential supports 72h. Also, the proximal and distal projections 877' and 877 are preferably sufficiently long such that the projections 877' and 877 of adjacent circumferential supports 72h axially overlap one another (e.g., the projections 877' extend within gaps defined between the projections 877, and the projections 877 extend within gaps between the projections 877'). By way of non-limiting example, the axial projections 877' and 877 can have lengths $l_5$ in the range of 0.005–0.010 inches, and an unloaded spacing $s_5$ in the range of 0.005–0.020 inches can exist between the circumferential supports 72h.

The axial projections 877' and 877 preferably provide two advantageous functions. First, as previously described, the axial projections 877' and 877 assist in transferring axial loads through the catheter segment 860 thereby enhancing axial stiffness. Also, the axial projections 877' and 877 cooperate to assist in transferring torque through the catheter segment 860. For example, when torque is applied to the catheter segment 860, the flexible outer jacket 90 is compressed between the proximal projections 877' and the axial projections 877 of adjacent circumferential supports 72h thereby increasing in the torsional stiffness of the catheter segment 860.

Figure 13A:
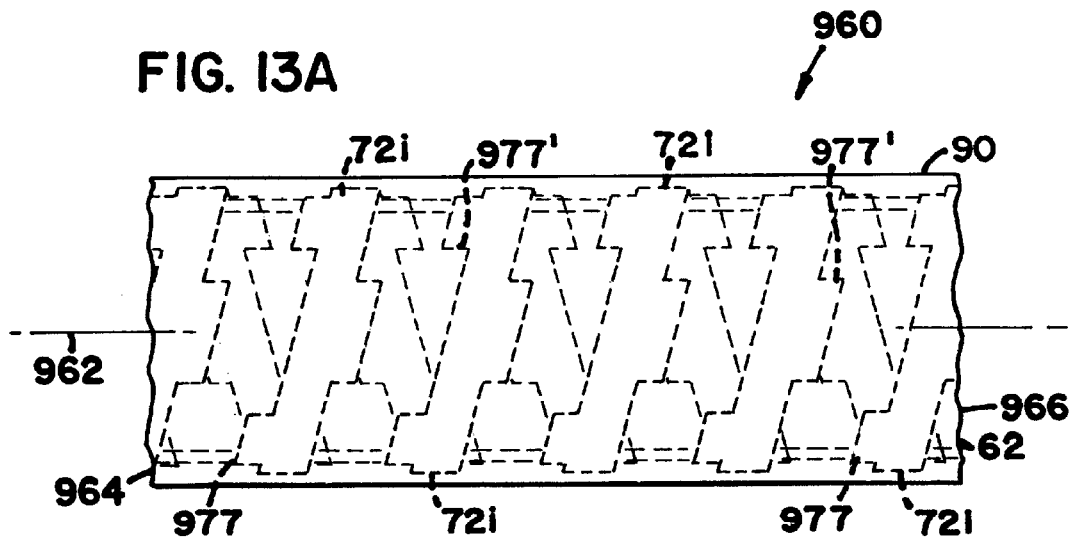
FIG. 13A is a side elevation view of a catheter segment having of a ninth embodiment of a circumferential support according to the present invention.

FIG. 13A shows a catheter segment 960 that is still another embodiment of the present invention. The catheter segment 960 includes circumferential supports 72i that are helically wound around a central longitudinal axis 962. The circumferential supports 72i are positioned between flexible inner liner 62 and flexible outer jacket 90. The catheter segment 960 includes a distal end 964 positioned opposite from a proximal end 966.

Axial projections, aligned generally parallel to the longitudinal axis 762, extend outward from the circumferential supports 72i. The axial projections include proximal projections 977' that extend longitudinally outward from proximal ends of the circumferential supports 72i and distal projections 977 that project longitudinally outward from distal ends of the circumferential supports 72i. The axial projections are circumferentially spaced about the longitudinal axis 962.

Figure 13B:
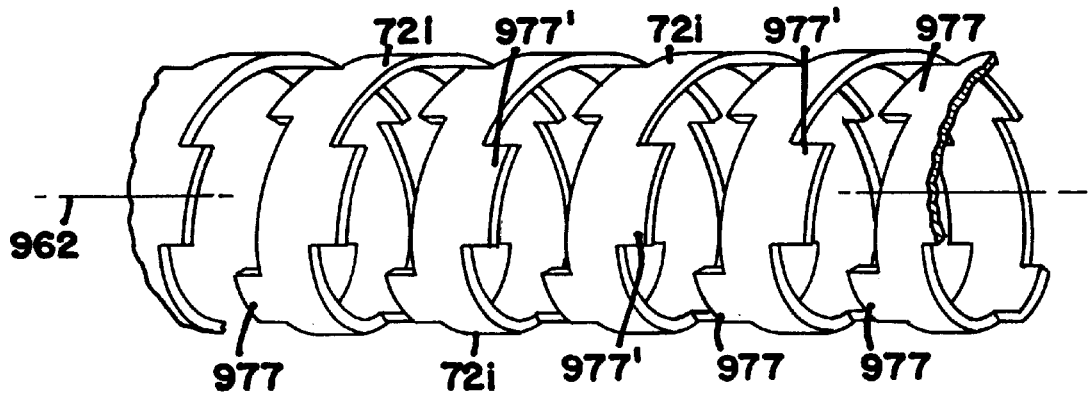
FIG. 13B is a perspective view of the circumferential support used by the embodiment of FIG. 13A in isolation from the catheter segment.

The distal projections 977 are circumferentially staggered relative to the proximal projections 977'. For example, as shown in FIG. 13B, the distal projections 977 are aligned generally between the proximal projections 977'. The distal and proximal projections 977 and 977' are generally rectangular in shape.

The distal and proximal projections 977 and 977' cooperate to increase the torsional stiffness of the catheter segment 960. For example, when torque is applied to the catheter segment 960, the flexible outer jacket 90 is compressed between the projections 977' and 977 of adjacent circumferential supports 72i thereby resisting rotation between adjacent circumferential supports 72i. The projections 977 and 977' also enhance the axial stiffness of the segment.

Figure 14A:
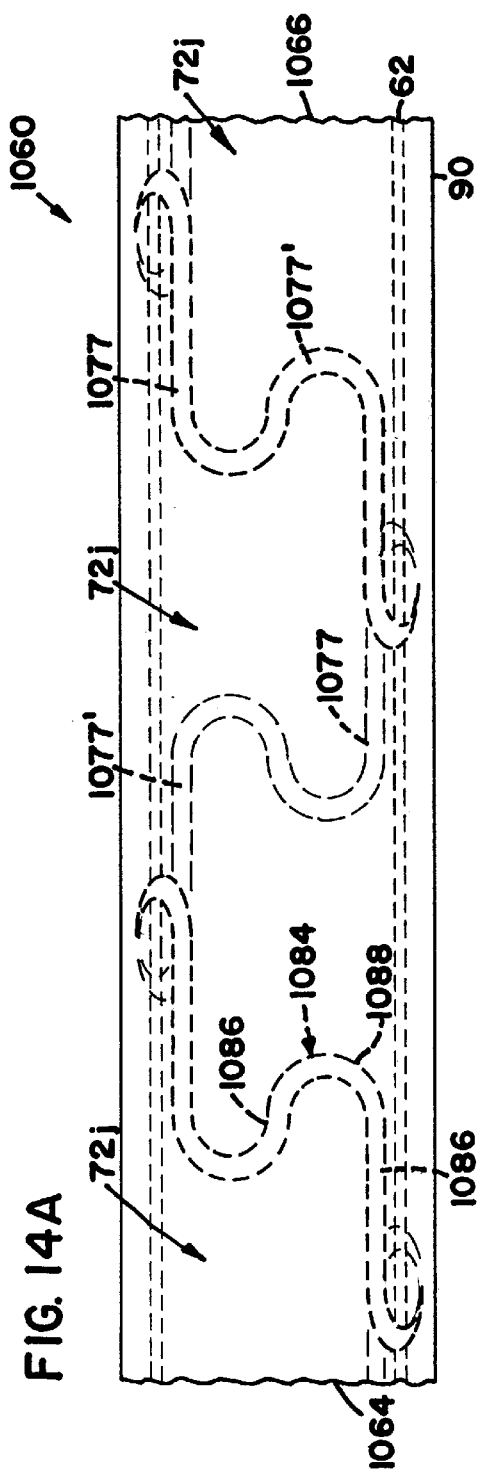
FIG. 14A is a side elevation view of a catheter segment having a tenth embodiment of a circumferential support according to the present invention.

FIG. 14A is a side view of a catheter segment 1060 that is still a further embodiment of the present invention. The catheter segment 1060 includes a plurality of circumferential supports 72j that are helically wrapped about a central longitudinal axis 1062 of the catheter segment 1060. The circumferential supports 72j are encapsulated between flexible inner liner 62 and outer jacket 90. The circumferential supports 72j are formed by a continuous helical slot 1084 that is filled with the material that forms the outer jacket 90. The slot 1084 has a generally serpentine configuration and includes longitudinal portions 1086 that are generally parallel to the longitudinal axis 1062, and circumferential portions 1088 that extend in a circumferential direction about the longitudinal axis 1062. The catheter segment 1060 includes a distal end 1064 positioned opposite from the proximal end 1066.

Figure 14B:
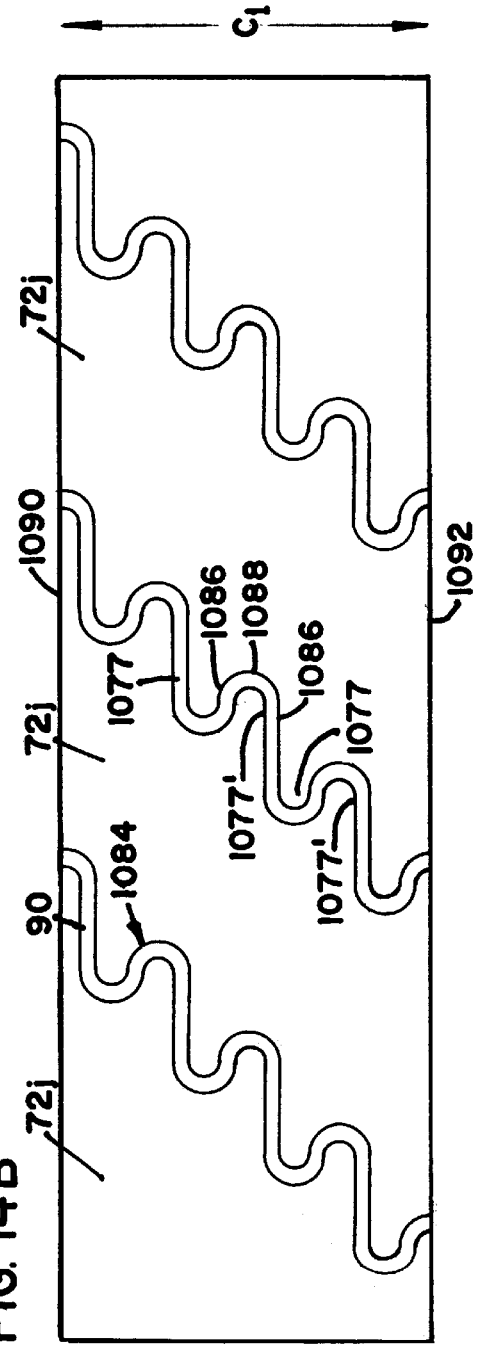
FIG. 14B is a plan view of a catheter segment of FIG. 14A, the catheter segment has been longitudinally cut and laid flat with the inner liner removed.

FIG. 14B is a plan view of the catheter segment 1060. In FIG. 14B, the catheter segment 1060 has been longitudinally cut and laid flat with the inner liner 62 removed to reveal the serpentine slot 1084. The catheter segment 1060 has a circumference $C_1$. When uncut, edge 1090 is intregally connected with edge 1092.

Referring back to FIG. 14B, the longitudinal and circumferential portions 1086 and 1088 of the serpentine slot 1084 cooperate to form proximal and axial projections or fingers 1077' and 1077 that extend longitudinally outward from the circumferential supports 72j. The proximal fingers 1077' fit between and axially overlap the axial fingers 1077 of adjacent circumferential supports 72j. The fingers 1077' and 1077 are separated by the portion of the flexible outer jacket 90 that fills the serpentine slot 1084.

The catheter segment 1060 utilizes circumferential supports 72j having a helical coil structure to resist kinking. The interlocking axial fingers 1077 and 1077' help to improve the torsional and axial stiffness of the catheter segment 1060. For example, when torque is applied to the catheter segment 1060, the fingers 1077 and 1077' from one circumferential support 72j interlock with the fingers 1077 and 1077' from the adjacent circumferential support to inhibit relative rotation between the supports 72j. Consequently, torque is transmitted through the structure of the catheter segment rather than being absorbed by the deformation of the helical circumferential support structure. Substantially the same action occurs when an axial load is applied to the catheter segment 1060. For example, the axial fingers or teeth 1077 and 1077' prevent the circumferential supports 72k from moving relative to one another thereby inhibiting the catheter segment from decreasing in diameter and inhibiting stretching of the catheter segment.

An additional advantage provided by the catheter segment 1060 is that the axial projections or teeth 1077 and 1077' help support the inner liner 62 of the catheter when the catheter is sharply bent. By supporting the inner liner 60, the catheter segment 1060 provides increased burst resistance.

Figure 15:
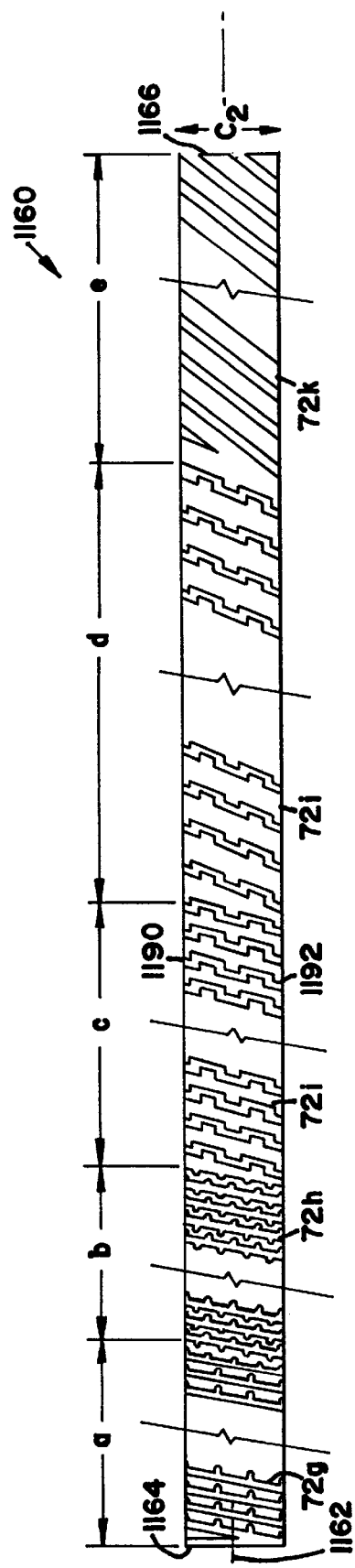
FIG. 15 is a plan view of a full length micro-catheter constructed in accordance with the principles of the present invention, the micro-catheter has been longitudinally cut and laid flat with the inner liner removed.

FIG. 15 illustrates a support structure for an entire full length microcatheter 1160 having varying degrees of flexibility. The support structure has been longitudinally cut and laid flat. Dimension $C_2$ represents a circumference of the support structure. When uncut, edges 1190 and 1192 are integrally connected and the support structure surrounds longitudinal axis 1162.

The catheter segment 1160 includes segments a, b, c, d, and e that extend progressively from a distal end 1164 to a proximal end 1166 of the catheter 1160. Segment a is preferably about 150 millimeters, segment b is preferably about 100 milliliters, segment c is preferably about 100 millimeters, segment d is preferably about 150 millimeters and segment e is preferably about 15 millimeters.

To vary the flexibility along the length of the catheter 1160, each segment a, b, c, d and e of the catheter 1160 has a different circumferential support configuration. For example, segment a has circumferential supports 72g similar to those shown in FIG. 11B, segment b has circumferential supports 72h similar to those shown in FIG. 12B, segment c has circumferential supports 72i similar to those shown in FIG. 13B, segment d has circumferential supports 72i' having an increased pitch angle and increased axial thickness as compared to the circumferential supports 72i, and segment e has standard helical coil circumferential supports 72k.

From the foregoing, the present invention has been disclosed in a preferred embodiment. The invention permits construction of a catheter overcoming disadvantages of prior designs as well as providing a structure having various features which can be modified to design catheters with optimum performance for a wide variety of applications. It is intended that modifications and equivalents of the disclosed concepts, such as those which readily occur to one of skill in the art shall be included within the scope of the claims appended hereto.

We claim:

1. A segment of a catherer, the catherer having a longitudinal axis extending between distal and proximal ends of the catherer, the segment comprising:
   a plurality of circumferential supports surrounding the longitudinal axis;
   axial members connected to the circumferential supports, the axial members extending in a direction generally along the longitudinal axis, and the axial members including free ends positioned between the circumferential supports, and the axial members having a generally cantilevered configuration; and
   a jacket covering the circumferential supports and the axial members, the circumferential supports and the axial members being embedded in the jacket.

2. The catheter segment of claim 1, wherein the axial members comprise axial projections having free ends that are rounded.

3. The catheter segment of claim 1, wherein the axial members comprise generally rectangular projections.

4. The catheter segment of claim 1, further comprising an resilient layer positioned generally between the circumferential supports.

5. The catheter segment of claim 1, wherein the circumferential supports comprise disjointed ring structures.

6. The catheter segment of claim 1, wherein the circumferential supports comprise helical coils.

7. The catheter segment of claim 1, wherein the axial members are circumferentially spaced about the circumferential supports.

8. The catheter segment of claim 1, wherein the circumferential supports include adjacent first and second circumferential supports and the axial members include first axial members connected to the first support and second axial members connected to the second support, the first axial members extending from the first circumferential support toward the second circumferential support, and the second axial members extending from the second circumferential support toward the first circumferential support.

9. The catheter segment of claim 8, wherein the first axial members are circumferentially staggered relative to the second axial members.

10. The catheter segment of claim 9, wherein the first axial members axially overlap the second axial members.

11. The catherer segment of claim 8, wherein the jacket comprises a resilient layer positioned between the first and second supports, wherein the resilient layer is compressed between the first and second axial members when a torque is applied to the catherer segment.

12. The catheter segment of claim 1, wherein the resilient layer is made of a polymeric material.

13. The catheter segment of claim 1, wherein the circumferential supports comprise helical rings formed by a slot cut through a tubular support member.

14. The catheter segment of claim 13, wherein the slot comprises a serpentine slot having first portions that extend generally along the longitudinal axis, and second portions that extend generally circumferentially about the longitudinal axis.

15. A segment of a catherer, the catherer having a longitudinal axis extending between distal and proximal ends of the catherer, the segment comprising:
   a generally tubular, flexible inner liner surrounding the longitudinal axis;
   first and second circumferential supports surrounding the inner liner and positioned adjacent to one another;
   first axial members having base ends connected to the first circumferential support, the first axial members extending from the first circumferential support toward the second circumferential support in a direction generally along the longitudinal axis, and the first axial members including free ends positioned opposite from the base ends of the first axial members;
   second axial members having base ends connected to the second circumferential support, the second axial members extending from the second circumferential support toward the first circumferential support in a direction generally aling the longitudinal axis, and the second axial members including free ends positioned opposite from the base ends of the second axial members; and
   a resilient layer covering the first and the second circumferential supports and the first and second axial members, the first and second circumferential supports and the first and second axial members being embedded in the resilient layer.

16. The catheter segment of claim 15, wherein the circumferential supports comprise disjointed rings.

17. The catheter segment of claim 15, wherein the circumferential supports comprise helical coils.

18. The catheter segment of claim 15, wherein the first axial members are circumferentially staggered with respect to the second axial members.

19. The catheter segment of claim 15, wherein the first and second axial members interlock.

20. The catheter segment of claim 15, wherein the first and second axial members axially overlap.

21. A segment of a catheter, the catheter having a longitudinal axis extending between distal and proximal ends of the catheter, the segment comprising:
   a plurality of circumferential supports surrounding the longitudinal axis;
   axial members connected to the circumferential supports, the axial members extending in a direction generally along the longitudinal axis, and the axial members including free ends; and
   the axial members being arranged and configured to provide means for compressing a polymeric layer thereinbetween when a torque is applied to the segment.

* * * * *